United States Patent
Sugiyama (10) Patent No.: US 8,388,975 B2
(45) Date of Patent: Mar. 5, 2013

(54) CANCER ANTIGEN PEPTIDES DERIVED FROM WT1

(75) Inventor: Haruo Sugiyama, Minoo (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 560 days.

(21) Appl. No.: 12/554,151

(22) Filed: Sep. 4, 2009

(65) Prior Publication Data

US 2010/0062013 A1 Mar. 11, 2010

Related U.S. Application Data

(63) Continuation of application No. 10/594,507, filed as application No. PCT/JP2005/006113 on Mar. 30, 2005, now Pat. No. 7,622,119.

(30) Foreign Application Priority Data

Mar. 31, 2004 (JP) .................................. 2004-105219

(51) Int. Cl.
*A61K 39/00* (2006.01)
(52) U.S. Cl. ................ 424/185.1; 424/193.1; 424/277.1
(58) Field of Classification Search .................. None
See application file for complete search history.

(56) References Cited

U.S. PATENT DOCUMENTS

| | | | |
|---|---|---|---|
| 7,030,212 B1 | 4/2006 | Sugiyama et al. | |
| 7,342,092 B2 | 3/2008 | Sugiyama | |
| 7,378,384 B2 | 5/2008 | Sugiyama et al. | |
| 7,390,871 B2 | 6/2008 | Sugiyama et al. | |
| 7,420,034 B2 | 9/2008 | Sugiyama et al. | |
| 7,517,950 B2 | 4/2009 | Sugiyama et al. | |
| 7,608,685 B1 | 10/2009 | Sugiyama et al. | |
| 7,622,119 B2 * | 11/2009 | Sugiyama ................. | 424/185.1 |
| 2003/0082194 A1 | 5/2003 | Gaiger et al. | |
| 2004/0097703 A1 | 5/2004 | Sugiyama | |
| 2004/0247609 A1 | 12/2004 | Sugiyama | |
| 2005/0002951 A1 | 1/2005 | Sugiyama et al. | |
| 2006/0217297 A1 | 9/2006 | Sugiyama et al. | |
| 2007/0128207 A1 | 6/2007 | Sugiyama | |
| 2008/0070835 A1 | 3/2008 | Sugiyama | |
| 2008/0152631 A1 | 6/2008 | Sugiyama | |
| 2009/0099090 A1 | 4/2009 | Sugiyama et al. | |
| 2009/0143291 A1 | 6/2009 | Sugiyama et al. | |
| 2009/0263409 A1 | 10/2009 | Sugiyama | |
| 2009/0281043 A1 | 11/2009 | Sugiyama et al. | |

FOREIGN PATENT DOCUMENTS

| | | |
|---|---|---|
| JP | 2002 525099 | 8/2002 |
| WO | 00 26249 | 5/2000 |
| WO | WO 01/25273 A2 | 4/2001 |
| WO | WO 03/037060 A2 | 5/2003 |

OTHER PUBLICATIONS

J. Konya, et al. "Identification of a cytotoxic T-lymphocyte epitope in the human papillomavirus type 16 E2 protein", Journal of General Virology, vol. 78, pp. 2615-2620 (1997).

Zinszner, H. et al., "Nucleotide Sequence of the HLA__A26 Class I Gene: Identification of Specific Residues and Molecular Mapping of Public HLA Class I Epitopes" Human Immunology, vol. 27, pp. 155-166, 1990.

(Continued)

*Primary Examiner* — Jeffrey E Russel (74) *Attorney, Agent, or Firm* — Oblon, Spivak, McClelland, Maier & Neustadt, L.L.P.

(57) ABSTRACT

The present invention relates to HLA-A26-binding cancer antigen peptides derived from WT1, polynucleotides encoding said peptide, CTL-inducers, and cancer vaccine comprising said peptide or polynucleotide.

6 Claims, 2 Drawing Sheets

OTHER PUBLICATIONS

Bellantuono, I. et al., "Two Distinct HLA-A0201-Presented Epitopes of the Wilms Tumor Antigen 1 Can Function as Targets for Leukemia-Reactive CTL" Blood, vol. 100, No. 10, pp. 3835-3837, 2002.

Liquan, G. et al., "Selective Elimination of Leukemic CD34+Progenitor Cells by Cytotoxic T Lymphocytes Specific for WT1", Blood, vol. 95, No. 7, pp. 2198-2203, 2000.

"Funakoshi News", Frontiers in Life Science, No. 2004 Nen 3 Gatsu 1 Nichi, pp. 1-13, 2004. (With English Translation).

Dal Porto, J. et al., "A Soluble Divalent Class I Major Histocompatibility Complex Molecule Inhibits Alloreactive T Cells at Nanomolar Concentrations", Proc. Natl, Acad. Sci. USA, vol. 90, pp. 6671-6675, 1993.

Call, K.M. et al., "Isolation and Characterization of a Zinc Finger Polypeptide Gene at the Human Chromosome 11 Wilms' Tumor Locus", Cell Press, vol. 60, pp. 509-520, 1990.

Gessler, M. et al., "Homozygous Deletion in Wilms Tumours of a Zinc-Finger Gene Identified by Chromosome Jumping", Letters to Nature, vol. 343, pp. 774-778, 1990.

Menke, A. L. et al., "The Wilms' Tumor 1 Gene: Oncogene or Tumor Suppressor Gene?" International Review of Cytology, vol. 181, pp. 151-212, 1998.

Sugiyama, H., "Cancer Immunotherapy Targeting WT1 Protein", International Journal of Hematology, vol. 76, pp. 127-132, 2002.

Akihiro Tsuboi, et al., "Enhanced Induction of Human WT1-Specific Cytotoxic T Lymphocytes With a 9-MER WT1 Peptide Modified at HLA-A*2402-Binding Residues", Cancer Immunology and Immunotherapy, XP 002961732, vol. 51, No. 11-12, Dec. 2002, 6 Pages.

Alexander Gaiger, et al., "Immunity to WT1 in the Animal Model and in Patients With Acute Myeloid Leukemia", Blood, XP 002965863, vol. 96, No. 4, Aug. 15, 2000, pp. 1480-1489.

Hideki Ohminami, et al., "HLA Class I-Restricted Lysis of Leukemia Cells by a CD8+ Cytotoxic T-lymphocyte Clone Specific for WT1 Peptide", Blood, XP 002190642, vol. 95, No. 1 Jan. 1, 2000, pp. 286-293.

U.S. Appl. No. 12/095,418, filed May 29, 2008, Nishihara, et al.
U.S. Appl. No. 12/552,660, filed Sep. 2, 2009, Sugiyama.
U.S. Appl. No. 12/280,268, filed Aug. 21, 2008, Sugiyama.
U.S. Appl. No. 12/521,533, filed Jun. 26, 2009, Sugiyama.
U.S. Appl. No. 12/449,765, filed Aug. 26, 2009, Sugiyama.
U.S. Appl. No. 12/529,701, filed Sep. 2, 2009, Sugiyama.

* cited by examiner

CANCER ANTIGEN PEPTIDES DERIVED FROM WT1

CROSS REFERENCE TO RELATED APPLICATIONS

This application is a continuation of allowed U.S. application Ser. No. 10/594,507, filed on Sep. 28, 2006, now U.S. Pat. No. 7,622,119, which is a 371 of International Patent Application No. PCT/JP05/06113, filed on Mar. 30, 2005, and claims priority to Japanese Patent Application No. 2004-105219, filed on Mar. 31, 2004.

TECHNICAL FIELD

The present invention relates to cancer antigen peptides derived from WT1 and their use.

BACKGROUND ART

WT1 gene (Wilms' tumor gene 1) has been identified as one of causative genes of Wilms' tumor that is a childhood renal tumor (*Cell* 60: 509, 1990, *Nature* 343: 774, 1990). WT1 gene encodes the transcription factor WT1, and WT1 plays an important role in many processes such as proliferation, differentiation and apoptosis of cells, and development of tissues (*Int. Rev. Cytol.* 181: 151, 1998). The WT1 gene was originally defined as a tumor suppressor gene. However, subsequent studies revealed that WT1 gene is expressed in leukemia and various solid cancers including lung cancer and breast cancer, indicating that WT 1 gene rather exerts an oncogenic function promoting cancer growth. In addition, it was demonstrated in vitro that, when peripheral blood mononuclear cells positive for HLA-A*0201 or HLA-A*2402 are stimulated with WT1-derived peptides, peptide-specific cytotoxic T-lymphocytes (CTLs) are induced and kill leukemia or solid tumor cells which endogenously express WT1. These results demonstrated that WT1 is a promising target molecule of cancer immunotherapy (*Int. J. Hematol* 76: 127, 2002). However, it has been neither elucidated whether said WT1 contains a peptide portion(s) capable of binding to HLA-A26 antigen nor reported that there is such a peptide(s).

In addition, although binding sequences for a cancer antigen peptide capable of binding to HLA-A*0201 (a member of HLA-A2 antigens) were deduced (WO 00/18795), only a few cancer antigen peptides have been proved to be effective so far (WO 00/06602 and WO 00/026249).

DISCLOSURE OF THE INVENTION

The purpose of the present invention is to provide cancer antigen peptides derived from WT1, their use as a CTL-inducer, and the like.

The present inventors have conducted intensive researches aiming at identification of novel cancer antigen peptides derived from WT1. As a result, it was revealed that peptides set forth in SEQ ID NOS: 2, 8 and 9 can induce HLA-A26-restricted CTLs. That is, the present inventors have for the first time found that WT1 contains a cancer antigen peptide portion(s) which binds to HLA-A26 antigen among a number of HLA antigen subclasses and is recognized by CTLs. This finding led to the development of novel cancer vaccine therapy which can induce WT1-specific CTLs in HLA-A26-positive cancer patients.

Furthermore, the present inventors have for the first time found that a peptide set forth in SEQ ID NO: 3 of which effects have been unknown has an activity, as a cancer antigen, of binding to HLA-A*0201 antigen and being recognized by CTLs.

The above-mentioned WT1-derived cancer antigen peptide and a polynucleotide encoding the same and the like of the present invention can be used effectively as a CTL inducer, namely cancer vaccine. In addition, the cancer antigen peptides of the present invention can be used effectively as an ingredient of a detecting agent for WT1-specific CTLs. The present invention has been established on the basis of these findings.

Thus, the present invention is related to:

(1) A peptide derived from the amino acid sequence of human WT1 set forth in SEQ ID NO: 1 and having activity as an HLA-A26-binding cancer antigen peptide;

(2) The peptide of (1) above, which comprises or consists of 8-11 contiguous amino acids in the amino acid sequence of human WT1 set forth in SEQ ID NO: 1;

(3) The peptide of (1) or (2) above, which comprises the amino acid sequence set forth in SEQ ID NO: 2, SEQ ID NO: 8 or SEQ ID NO: 9;

(4) A tumor antigen peptide consisting of the amino acid sequence set forth in SEQ ID NO: 2, SEQ ID NO: 8 or SEQ ID NO: 9;

(5) An epitope peptide comprising a peptide described in any one of (1) to (4) above;

(6) A polynucleotide encoding a peptide described in any one of (1) to (5) above;

(7) An expression vector containing the polynucleotide described in (6) above;

(8) A cell containing the expression vector described in (7) above;

(9) A process for producing a peptide described in any one of (1) to (5) above, which comprises culturing the cell described in (8) above under the condition where the peptide can be expressed;

(10) An antibody which specifically binds to a peptide described in any one of (1) to (4) above;

(11) An antigen-presenting cell on which a complex between an HLA-A26-binding cancer antigen peptide derived from the amino acid sequence of human WT1 set forth in SEQ ID NO: 1, preferably a peptide described in any one of (2) to (4) above and an HLA-A26 antigen is presented;

(12) A CTL which recognizes a complex between an HLA-A26-binding cancer antigen peptide derived from the amino acid sequence of human WT1 set forth in SEQ ID NO: 1, preferably a peptide described in any one of (2) to (4) above and an HLA-A26 antigen;

(13) A pharmaceutical composition which comprises a peptide described in any one of (1) to (5) above, an expression vector described in (7) above, a cell described in (8) above, an antigen-presenting cell described in (11) above, or a CTL described in (12) above, together with a pharmaceutically acceptable carrier;

(14) The pharmaceutical composition of (13) above, which is used as a CTL inducer;

(15) The pharmaceutical composition of (13) above, which is used as cancer vaccine;

(16) An HLA monomer, dimer, tetramer or pentamer comprising an HLA-A26-binding cancer antigen peptide derived from the amino acid sequence of human WT1 set forth in SEQ ID NO: 1, preferably a peptide described in any one of (2) to (4) above, together with an HLA-A26 antigen;

(17) A reagent for the detection of CTLs specific for an HLA-A26-binding cancer antigen peptide derived from WT1, which reagent comprises an HLA monomer, dimer, tetramer or pentamer described in (16) above as an ingredient;

(18) A pharmaceutical composition which comprises any one of the following a) to f) together with a pharmaceutically acceptable carrier:
    a) a peptide comprising the amino acid sequence set forth in SEQ ID NO: 3 or SEQ ID NO: 4,
    b) an epitope peptide comprising the peptide of a) above,
    c) an expression vector containing a polynucleotide encoding the peptide of a) or b) above,
    d) a cell containing the expression vector of c) above,
    e) an antigen-presenting cell on which a complex between the peptide of a) above and an HLA-A*0201 antigen is presented, and
    f) a CTL which recognizes the complex between the peptide of a) and an HLA-A*0201 antigen;
(19) The pharmaceutical composition of (18) above, which is used as a CTL inducer;
(20) The pharmaceutical composition of (19) above, which is used as cancer vaccine;
(21) An HLA monomer, dimer, tetramer or pentamer which comprises a peptide comprising the amino acid sequence set forth in SEQ ID NO: 3 or SEQ ID NO: 4 together with an HLA-A*0201 antigen; or
(22) A reagent for the detection of CTLs specific for HLA-A*0201-binding cancer antigen peptide derived from WT1, which reagent comprises an HLA monomer, dimer, tetramer or pentamer described in (21) above as an ingredient.

The present invention provides cancer antigen peptides derived from WT1, polynucleotides encoding the same, CTL-inducers comprising the same, and the like. The CTL inducer of the present invention is useful as cancer vaccine. The cancer vaccine of the present invention is applicable to many cancer patients who are positive for HLA-A26 or HLA-A*0201.

BEST MODE FOR CARRYING OUT THE INVENTION

The present invention provides a peptide which is derived from the amino acid sequence of human WT1 set forth in SEQ ID NO: 1 and has activity as an HLA-A26-binding cancer antigen peptide.

The amino acid sequence of human WT1 set forth in SEQ ID NO: 1 is a known sequence (*Cell*, 60: 509, 1990, NCBI database Accession No. XP_034418 and Accession No. P19544). The said amino acid sequence of human WT1 is shown in SEQ ID NO: 1. As HLA-A26 antigens, HLA-A*2601, HLA-A*2602, HLA-A*2603 and the like are known. For the present invention, preferred HLA-A26 antigen is HLA-A*2601. In Japan, about 20% of population share HLA-A26 antigen among HLA antigens.

It was for the first time found that the amino acid sequence of WT1 contains cancer antigen peptide portions capable of binding to HLA-A26 antigen and being recognized by CTLs, which led to the establishment of the present invention.

In the context of the present invention, the term "having (have) activity as an HLA-A26 binding cancer antigen peptide" means that a peptide has an activity of binding to HLA-A26 antigen and being recognized by cytotoxic T cells (CTLs), and is synonym for "binding to HLA-A26 antigen and inducing CTLs (having a CTL-inducing activity)", or "binding to HLA-A26 antigen and activating CTLs (having a CTL-activating activity)".

Accordingly, the phrase "peptide derived from the amino acid sequence of human WT1 set forth in SEQ ID NO: 1 and having activity as an HLA-A26-binding cancer antigen peptide" refers to a peptide which comprises a cancer antigen peptide consisting of a portion of the amino acid sequence of WT1 set forth in SEQ ID NO: 1 and is capable of binding to HLA-A26 antigen and being recognized by CTLs, inclusive of the said cancer antigen peptide itself. The cancer antigen peptide of the present invention can be any peptide so long as it consists of a portion of amino acid sequence of human WT1 set forth in SEQ ID NO: 1 and has activity as an HLA-A26 (HLA-A26 antigen)-binding cancer antigen peptide. The length of cancer antigen peptides is preferably 8-11 amino acids, more preferably 9-10 amino acids. Peptides having activity as a cancer antigen peptide of the present invention may have one or more additional amino acids at the N- or C-terminus. When a peptide of the present invention has an additional amino acid(s), the entire length of the peptide is generally contiguous 8-100 amino acids, preferably contiguous 8-50 amino acids, and more preferably contiguous 8-30 amino acids.

The cancer antigen peptide of the present invention can be identified by synthesizing a partial peptide (candidate peptide) consisting of 8-11 contiguous amino acids in the amino acid sequence set forth in SEQ ID NO: 1, and assaying whether or not the peptide has activity as an HLA-A26-binding cancer antigen peptide.

The synthesis of peptides can be conducted according to a method generally used in the field of peptide chemistry. Such a method can be found in literatures including *Peptide Synthesis*, Interscience, New York, 1966; *The Proteins*, Vol. 2, Academic Press Inc., New York, 1976; *Peptide Synthesis*, Maruzen, Inc., 1975; *Peptide-Gosei no Kiso to Jikken*, Maruzen, Inc., 1985; and *Iyakuhin no Kaihatsu* (Zoku), Vol. 14, Peptide Synthesis, Hirokawa-syoten, 1991.

It can be examined whether or not a candidate peptide is the HLA-A26-binding cancer antigen peptide by a method described in, for example, *Tissue Antigen* 61: 136. 2003, or a method described in the working Examples below. It can also be examined whether or not a candidate peptide is a peptide having activity as an HLA-A26-binding cancer antigen peptide in a similar manner.

Specifically, peripheral blood mononuclear cells (PBMCs) are firstly isolated from a human subject positive for HLA-A26 antigen and cultured after adding (pulsing with) a candidate peptide. After cultivation, the culture is repeatedly stimulated several times by adding a peptide every few days to amplify CTLs specific for the peptide. Then peptide-specific reaction of said CTLs is detected by measuring cytokines such as IFN-γ produced by CTLs or cytotoxic activity of CTLs. The cytotoxic activity can be measured by, for example, $^{51}$Cr release assay (*Int. J. Cancer*, 58: p 317, 1994) or the like. Examples of target cell usable in the assay include $^{51}$Cr-labeled cells which are positive for WT1 and positive for HLA-A26. Specific examples include $^{51}$Cr-labeled cells which are obtained by introducing a gene encoding HLA-A26 gene (e.g., Genbank Accession No. D14350) into a leukemia cell line which is positive for WT1 and negative for HLA-A26.

When the results of assay above show that CTLs kill the target cells or produce cytokines, the said candidate peptide is identified to be "an HLA-A26-binding cancer antigen peptide" or "a peptide having activity as an HLA-A26 binding cancer antigen peptide".

Examples of specific embodiments of a peptide having activity as an HLA-A26-binding cancer antigen peptide of the present invention include a peptide comprising the amino acid sequence set forth in SEQ ID NO: 2, 8, 9, 10, 11, 12, 13, 14 or 15, and has activity as an HLA-A26-binding cancer antigen peptide. Preferably, the present invention provides a peptide comprising the amino acid sequence set forth in SEQ ID NO: 2, 8 or 9. There are no limitations regarding the length of such a peptide on the condition that said peptide has the activity of binding to HLA-A26 antigen and being recognized by CTLs. However, a peptide (cancer antigen peptide) having a binding activity to HLA antigen is known to generally consist of 8 to 11 amino acids. Accordingly, the cancer antigenic peptide portion in the peptide of the present invention comprising the amino acid sequence set forth in SEQ ID NO: 2, 8, 9, 10, 11, 12, 13, 14 or 15 is a peptide preferably consisting of 9-11 amino acids, more preferably, 9-10 amino acids. Still more preferably, it is a cancer antigen peptide consisting of the amino acid sequence set forth in SEQ ID NO: 2, 8, 9, 10, 11, 12, 13, 14 or 15, and most preferably, a cancer antigen peptide consisting of the amino acid sequence set forth in SEQ ID NO: 2, 8 or 9.

The peptides of the present invention may be altered as appropriate within a range that the activity is maintained. As used herein the "alteration" of amino acid residue means substitution, deletion and/or addition of an amino acid residue(s) (the addition is inclusive of addition of amino acid(s) at the N- and/or C-terminus of peptide). The substitution of an amino acid residue(s) is preferred. When the alteration involves substitution of an amino acid residue(s), any number of amino acid residues at any position can be replaced on the condition that the activity as cancer antigen peptide is retained. However, since a peptide which binds to HLA antigen is generally about 8-11 amino acid in length, the alteration is preferably involves one to several amino acids.

The present invention also provides a peptide (so-called an epitope peptide) comprising a peptide of the present invention together with a helper peptide or another cancer antigen peptide.

Recently, a peptide ("epitope peptide") composed of multiple (plural) CTL epitopes (antigen peptides) linked together has been shown to have an activity of inducing CTLs efficiently. For example, it has been reported that a peptide (about 30-mer) wherein CTL epitopes each restricted to HLA-A2-, -A3, -A11 or B53 originated from cancer antigen protein PSA are ligated together induced in vivo CTLs specific for respective CTL epitopes (*Journal of Immunology* 1998, 161: 3186-3194).

In addition, a peptide (epitope peptide) wherein a CTL epitope(s) and a helper epitope(s) are ligated has been shown to induce CTLs efficiently. In this context, "helper epitope" means a peptide capable of activating a CD4-positive T cells (*Immunity.*, 1:751, 1994), and examples thereof include HBVc128-140 of hepatitis B virus origin, TT947-967 of tetanus toxin origin, etc. CD4$^+$ T cells activated by said helper epitope exert various activities including induction and maintenance of CTLs, differentiation, and activation of effectors such as macrophages, etc., and hence are considered to be important in the immunological anti-tumor response. As a concrete example of a peptide wherein a helper epitope(s) and CTL epitope(s) are linked together, it is reported that a DNA (minigene) encoding a peptide composed of HBV-originated HLA-A2-restricted antigen peptides (6 peptides), HLA-A11-restricted antigen peptides (3 peptides) and a helper epitope induced in vivo CTLs directed to the respective epitopes efficiently (*Journal of Immunology* 1999, 162: 3915-3925). Practically, a peptide wherein a CTL epitope (tumor antigen peptide corresponding to position 280-288 of melanoma antigen gp100) and a helper epitope (tetanus toxin-originated T helper epitope) are ligated has been subjected to clinical test (*Clinical Cancer Res.*, 2001, 7:3012-3024).

Accordingly, as a specific embodiment, the peptides of the present invention also include epitope peptides in which multiple epitopes including the aforementioned peptides of the present invention are ligated and which have a CTL-inducing activity.

When the epitope to be ligated to the cancer antigen peptide of the present invention is a CTL epitope (cancer antigen peptide), examples of CTL epitopes usable include WT1-derived CTL epitopes capable of binding to HLA-A*0201, -A*0204, -A*0205, -A*0206, -A*0207, -A11, -A24, -A31, -A*6801, -B7, -B8, -B*2705, -B37, -Cw*0401 or -Cw*0602 (*Int. J. Hematol* 76: 127, 2002; *Int. J. Hematol* 78: 56, 2003, WO 00/06602, WO 00/18795). Plural numbers of these CTL epitopes can be linked together, and the length of one CTL epitope may be about 8-14 amino acids on the basis of the analysis of antigen peptides bound to various HLA molecules (*Immunogenetics*, 41: 178, 1995).

When the epitope to be ligated to the cancer antigen peptide of the present invention is a helper epitope, examples of helper epitopes usable include the aforementioned HBVc128-140 of hepatitis B virus origin, TT947-967 of tetanus toxin origin, a WT1-derived helper epitope (Lys Arg Tyr Phe Lys Leu Ser His Leu Gln Met His Ser Arg Lys His, SEQ ID NO: 5), and the like. The helper epitope may be about 13-30 amino acids, preferably, about 13-17 amino acids in length.

Specifically, examples of epitope peptides of the present invention include an epitope peptide which comprises a peptide consisting of the amino acid sequence set forth in SEQ ID NO: 2, 8, 9, 10, 11, 12, 13, 14 or 15 and a helper peptide, preferably an epitope peptide which comprises a peptide consisting of the amino acid sequence set forth in SEQ ID NO: 2, 8 or 9 and a helper peptide.

More specifically, examples include an epitope peptide which comprises a peptide consisting of the amino acid sequence set forth in SEQ ID NO: 2, 8, 9, 10, 11, 12, 13, 14 or 15, preferably a peptide consisting of the amino acid sequence set forth in SEQ ID NO: 2, 8 or 9 and a peptide consisting of the amino acid sequence set forth in SEQ ID NO: 5; an epitope peptide which comprises a peptide consisting of the amino acid sequence set forth in SEQ ID NO: 2, 8, 9, 10, 11, 12, 13, 14 or 15, preferably a peptide consisting of the amino acid sequence set forth in SEQ ID NO: 2, 8 or 9 and a tetanus toxin-originated helper peptide (e.g., Phe Asn Asn Phe Thr Val Ser Phe Trp Leu Arg Val Pro Lys Val Ser Ala Ser His Leu Glu, SEQ ID NO: 6); and an epitope peptide which comprises a peptide consisting of the amino acid sequence set forth in SEQ ID NO: 2, 8, 9, 10, 11, 12, 13, 14 or 15, preferably a peptide consisting of the amino acid sequence set forth in SEQ ID NO: 2, 8 or 9 and a peptide (Ala Gln Tyr Ile Lys Ala Asn Ser Lys Phe Ile Gly Ile Thr Glu Leu, SEQ ID NO: 7; *Clinical Cancer Res.,* 2001,7:3012-3024).

The peptide (epitope peptide) wherein multiple epitopes are ligated can be prepared by a usual method for peptide synthesis as described above. It is also obtainable by a usual method for DNA synthesis and genetic engineering on the basis of sequence information of a polynucleotide encoding an epitope peptide wherein multiple epitopes are ligated. Specifically, an epitope peptide wherein a multiple epitopes are ligated can be prepared by inserting said polynucleotide into a known expression vector, transforming a host cell with the resultant recombinant expression vector, culturing the resultant transformed cells, and recovering the objective epitope peptide wherein multiple epitopes are ligated from the culture. These processes can be conducted according to, for example, a method described in a literature (*Molecular Cloning*, T. Maniatis et al., CSH Laboratory (1983), *DNA Cloning*, D M. Glover, IRL PRESS (1985)), or the method described hereinafter.

The CTL-inducing activity of the so produced epitope peptide wherein multiple epitopes are ligated can be examined by subjecting to, for example, the above-mentioned $^{51}$Cr release assay.

The above-described peptides (including epitope peptides) of the present invention can be modified at the amino group of the N-terminal amino acid and/or at the carboxyl group of the C-terminal amino acid. Thus, peptides wherein the N-terminal and/or the C-terminal amino acid residue is modified fall within the scope of the peptide of the present invention.

Examples of a group for the modification of amino group of the N-terminal amino acid include 1 to 3 groups selected from $C_{1-6}$ alkyl group, phenyl group, cycloalkyl group and acyl group. Acyl groups include $C_{1-6}$ alkanoyl group, $C_{1-6}$ alkanoyl group substituted by phenyl group, carbonyl group substituted by $C_{5-7}$ cycloalkyl group, $C_{1-6}$ alkylsulfonyl group, phenylsulfonyl group, $C_{2-6}$ alkoxycarbonyl group, alkoxycarbonyl group substituted by phenyl group, carbonyl group substituted by $C_{5-7}$ cycloalkoxy group, phenoxycarbonyl group, and the like.

Examples of peptides modified at the carboxyl group of the C-terminal amino acid include esters and amides. Esters include $C_{1-6}$ alkyl esters, $C_{0-6}$ alkyl esters substituted by phenyl group, $C_{5-7}$ cycloalkyl esters, and the like. Amides specifically include amides, amides substituted by one or two $C_{1-6}$ alkyl groups, amides substituted by one or two $C_{0-6}$ alkyl groups that are substituted by phenyl group, amides forming 5- to 7-membered azacycloalkane inclusive of nitrogen atom of amide group, and the like.

The present invention also provides a polynucleotide encoding the above-mentioned peptide of the present invention. The polynucleotide encoding a peptide of the present invention may be in the form of DNA or RNA. The polynucleotides of the present invention can be easily prepared on the basis of information about amino acid sequence of the present peptide or polynucleotide sequence of DNA encoding the same. Specifically, synthesis can be carried out using usual method of DNA synthesis or amplification by PCR.

In particular, examples include a polynucleotide encoding an epitope peptide which comprises a peptide consisting of the amino acid sequence set forth in SEQ ID NO: 2, 8, 9, 10, 11, 12, 13, 14 or 15, preferably a peptide consisting of the amino acid sequence set forth in SEQ ID NO: 2, 8 or 9 and a helper epitope.

Preferred examples include a polynucleotide encoding an epitope peptide which comprises a peptide consisting of the amino acid sequence set forth in SEQ ID NO: 2, 8, 9, 10, 11, 12, 13, 14 or 15, more preferably a peptide consisting of the amino acid sequence set forth in SEQ ID NO: 2, 8 or 9 and a peptide consisting of the amino acid sequence set forth in SEQ ID NO: 5; a polynucleotide encoding an epitope peptide which comprises a peptide consisting of the amino acid sequence set forth in SEQ ID NO: 2, 8, 9, 10, 11, 12, 13, 14 or 15, more preferably a peptide consisting of the amino acid sequence set forth in SEQ ID NO: 2, 8 or 9 and a tetanus toxin-originated helper peptide (e.g., Phe Asn Asn Phe Thr Val Ser Phe Trp Leu Arg Val Pro Lys Val Ser Ala Ser His Leu Glu, SEQ ID NO: 6); and a polynucleotide encoding an epitope peptide which comprises a peptide consisting of the amino acid sequence set forth in SEQ ID NO: 2, 8, 9, 10, 11, 12, 13, 14 or 15, more preferably a peptide consisting of the amino acid sequence set forth in SEQ ID NO: 2, 8 or 9 and a peptide (Ala Gln Tyr Ile Lys Ala Asn Ser Lys Phe Ile Gly Ile Thr Glu Leu, SEQ ID NO: 7; *Clinical Cancer Res.,* 2001,7: 3012-3024).

A recombinant expression vector for expressing the peptide of the present invention can be constructed by incorporating a polynucleotide prepared in the above into an expression vector.

An adequate expression vector can be selected depending on the host to be used, purposes, and the like, and include plasmids, phage vectors, virus vectors, and the like.

When the host is *Escherichia coli*, examples of vector include plasmid vectors such as pUC118, pUC119, pBR322, pCR3, and the like; and phage vectors such as λZAPII, λgt11, and the like. When the host is yeast, examples of vector include pYES2, pYEUra3, and the like. When the host is insect cells, examples of vector include pAcSGHisNT-A, and the like. When the host is animal cells, examples of vector include plasmid vectors such as pKCR, pCDM8, pGL2, pcDNA3.1, pRc/RSV, pRc/CMV, and the like; and virus vectors such as retrovirus vector, adenovirus vector, adeno-associated virus vector, and the like.

The expression vectors above may optionally contain a factor(s) such as promoter capable of inducing expression (expression-inducing promoter), a gene encoding a signal sequence, a marker gene for selection, terminator, and the like.

Furthermore, the expression vector may contain an additional sequence for expressing the peptide as a fusion protein with thioredoxin, His tag, GST (glutathione S-transferase), or the like, so as to facilitate the isolation and purification. Vectors usable in such a case include GST fusion protein vectors containing an appropriate promoter (lac, tac, trc, trp, CMV, SV40 early promoter, etc) that functions in host cells, such as pGEX4T; vectors containing Tag sequence (Myc, His, etc) such as pcDNA3.1/Myc-His; and vectors capable of expressing a fusion protein with thioredoxin and His tag such as pET32a.

Transformed cells containing the vector of the present invention can be prepared by transforming host cells with an expression vector obtained in the above.

Host cells usable herein include *Escherichia coli*, yeast, insect cells and animal cells. Examples of *Escherichia coli* include strains of *E. coli* K-12 such as HB101, C600, JM109, DH5α and AD494 (DE3). Examples of yeast include *Saccharomyces cerevisiae*. Examples of animal cells include L929, BALB/c3T3, C127, CHO, COS, Vero and Hela cells. Examples of insect cells include sf9.

Introduction of an expression vector into host cells can be conducted using a conventional method suited for the respective host cells above. Specifically, introduction can be conducted using calcium phosphate method, DEAE-dextran method, electroporation method, and a method using lipid for gene transfer (Lipofectamine, Lipofectin; Gibco-BRL). Transformed cells containing the expression vector can be selected by culturing the host cells after introduction in a conventional medium containing a selection marker.

The peptide of the present invention can be produced by culturing the transformed cells under appropriate conditions (conditions under which peptides can be expressed). The resultant peptide may be further isolated and purified according to standard biochemical purification procedures. The purification procedures include salting out, ion exchange chromatography, absorption chromatography, affinity chromatography, gel filtration chromatography, and the like. When the polypeptide of the present invention has been expressed as a fusion peptide with thioredoxin, His tag, GST, or the like, as mentioned above, the peptide can be isolated and purified by appropriate purification procedures making use of the characteristics of the fusion protein or tags.

The present invention provides an antibody which specifically binds to a peptide of the present invention. The antibody of the present invention is not restricted to any form and may be polyclonal or monoclonal antibody raised against a peptide of the present invention as an antigen.

As mentioned above, there is no limitation regarding the antibody of the present invention on the condition that it specifically binds to a peptide of the present invention. Examples of antibody include those specifically bind to a peptide consisting of the amino acid sequence set forth in SEQ ID NO: 2, 8, 9, 10, 11, 12, 13, 14 or 15, preferably to a peptide consisting of the amino acid sequence set forth in SEQ ID NO: 2, 8 or 9.

Methods of preparation of antibodies are well known in the art and the antibodies of the present invention can be prepared by such conventional methods (*Current protocols in Molecular Biology* edit. Ausubel et al. (1987) Publish. John Wiley and Sons. Section 11.12-11.13, Antibodies; *A Laboratory Manual*, Lane, H, D. et al., ed., Cold Spring Harber Laboratory Press, New York 1989).

Specifically, antibodies can be prepared by immunizing a non-human animal such as rabbit with a peptide of the present invention as an antigen, and recovering antibodies from serum of the immunized animal in a conventional manner. On the other hand, monoclonal antibodies can be obtained by immunizing a non-human animal such as mouse with a peptide of the present invention, subjecting the resultant splenocytes to cell fusion with myeloma cells, and recovering antibodies from the resultant hybridoma cells (*Current protocols in Molecular Biology* edit. Ausubel et al. (1987) Publish. John Wiley and Sons. Section 11.4-11.11).

The antibodies against the peptide of the present invention can also be produced while enhancing the immunological response using different adjuvants depending on the host. Examples of adjuvants include Freund adjuvants; mineral gels such as aluminium hydroxide; surfactants such as lysolecithin, Pluronic polyol, polyanion, peptide, oil emulsion, keyhole limpet hemocyanin and dinitorophenol; human adjuvants such as BCG (Bacille de Calmette-Guerin) or *Corynebacterium*, and the like.

As mentioned above, antibodies that recognize a peptide of the present invention and antibodies that neutralize the activity thereof can be easily prepared by immunizing an animal with a peptide of the present invention appropriately in a conventional manner. The antibodies may be used in affinity chromatography, immunological diagnostic method, and the like. Immunological diagnostic method may be selected as appropriate from immunoblotting, radioimmunoassay (RIA), enzyme-linked immunosorbent assay (ELISA), a fluorescent or luminescent assay, and the like. The immunological diagnostic method is effective in the diagnosis of cancer accompanied by elevated expression of WT1, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

The present invention provides an antigen-presenting cell which presents a complex between a peptide of the present invention and an HLA-A26 antigen.

As shown in the Examples below, stimulation with a peptide of the present invention induced CTLs, which indicates that there existed antigen-presenting cells presenting a complex between a peptide of the present invention and an HLA-A26 antigen and that CTLs specifically recognizing said antigen-presenting cells were induced. Such antigen-presenting cells presenting a complex between a peptide of the present invention and an HLA-A26 antigen are used effectively in the cell therapy (DC therapy) as hereinafter described.

The antigen-presenting cells of the present invention include any cells presenting a complex of an HLA-A26 antigen and a cancer antigen peptide of the present invention, and specific examples include antigen-presenting cells wherein a complex between a peptide consisting of the amino acid sequence set forth in SEQ ID NO: 2, 8, 9, 10, 11, 12, 13, 14 or 15, preferably a peptide consisting of the amino acid sequence set forth in SEQ ID NO: 2, 8 or 9 and an HLA-A26 antigen is presented on the cell surface of dendritic cells.

The antigen-presenting cells used in the cell therapy (DC therapy) can be prepared by isolating cells having antigen-presenting ability from a cancer patient, pulsing the cells in vitro with a peptide of the present invention, or introducing into the cells a polynucleotide or an expression vector containing the same of the present invention, and allowing the cells to present a complex between an HLA-A26 antigen and a cancer antigen peptide of the present invention on the cell surface. The "cells having antigen-presenting ability" are not limited to particular cells and may be any cells expressing HLA-A26 antigen capable of presenting a peptide of the present invention on the cell surface; however, dendritic cells known to have especially high antigen-presenting ability are preferred.

Further, the substance with which cells having antigen-presenting ability above are pulsed may be a peptide of the present invention, or a polynucleotide encoding the peptide of the present invention or an expression vector containing the same.

The antigen-presenting cells of the present invention can be prepared by, for example, isolating cells having antigen-presenting ability from a cancer patient, pulsing the cells in vitro with a peptide of the present invention (e.g., a cancer antigen peptide consisting of the amino acid sequence set forth in SEQ ID NO: 2, 8, 9, 10, 11, 12, 13, 14 or 15, preferably a cancer antigen peptide consisting of the amino acid sequence set forth in SEQ ID NO: 2, 8 or 9), thereby producing a complex between an HLA-A26 antigen and the peptide of the present invention (*Cancer Immunol. Immunother.*, 46:82, 1998, *J. Immunol.*, 158: p 1796,1997, *Cancer Res.*, 59: p 1184, 1999). When dendritic cells are used, antigen-presenting cells of the present invention can be prepared by, for example, isolating lymphocytes from peripheral blood of a cancer patient by Ficoll method, removing non-adherent cells, incubating the adherent cells in the presence of GM-CSF and IL-4 to induce dendritic cells, and pulsing the dendritic cells by incubating with a peptide of the present invention.

In the case where antigen-presenting cells of the present invention are prepared by introducing a polynucleotide encoding a peptide of the present invention (e.g., a polynucleotide encoding an epitope peptide which comprises the amino acid sequence set forth in SEQ ID NO: 2, 8, 9, 10, 11, 12, 13, 14 or 15, preferably the amino acid sequence set forth in SEQ ID NO: 2, 8 or 9) or an expression vector containing the same into the above-mentioned cells having an antigen-presenting ability, the preparation can be carried out referring to a method described in *Cancer Res.*, 56:p 5672, 1996 or *J. Immunol.*, 161:p 5607, 1998, or the like, when the polynucleotide is DNA. The preparation of antigen-presenting cells can be effected using RNA as well as DNA in a similar manner, referring to *J. Exp. Med.*, 184: p 465, 1996, or the like.

The present invention also provides CTLs which recognize a complex between a cancer antigen peptide of the present invention and an HLA-A26 antigen.

As shown in the Examples below, stimulation with a peptide of the present invention resulted in the CTL-inducing activity. This indicates that there existed antigen-presenting cells presenting a complex between a peptide of the present invention and an HLA-A26 antigen and that CTLs specifically recognizing said antigen-presenting cells were induced. Such CTLs which specifically recognize a complex between an HLA-A26 antigen and a peptide of the present invention can be used effectively in the adoptive immunotherapy as hereinafter described.

CTLs of the present invention may be in any form on the condition that they recognize specifically a complex of a peptide of the present invention with an HLA-A26 antigen, and include a monoclonal CTL and CTL mixture (population) comprising different kinds of clones. In particular, examples include CTLs specifically recognize a complex of a peptide consisting of the amino acid sequence set forth in SEQ ID NO: 2, 8, 9, 10, 11, 12, 13, 14 or 15, preferably a peptide consisting of the amino acid sequence set forth in SEQ ID NO: 2, 8 or 9 with an HLA-A26 antigen.

CTLs used in the adoptive immunotherapy can be prepared by isolating peripheral blood lymphocytes from a patient, stimulating the cells in vitro with a peptide of the present invention (e.g., a cancer antigen peptide consisting of the amino acid sequence set forth in SEQ ID NO: 2, 8, 9, 10, 11, 12, 13, 14 or 15, preferably a cancer antigen peptide consisting of the amino acid sequence set forth in SEQ ID NO: 2, 8 or 9), or a polynucleotide encoding a peptide of the present invention (e.g., a polynucleotide encoding an epitope peptide comprising the amino acid sequence set forth in SEQ ID NO: 2, 8, 9, 10, 11, 12, 13, 14 or 15, preferably the amino acid sequence set forth in SEQ ID NO: 2, 8 or 9), or an expression vector containing the same (*Journal of Experimental Medicine* 1999, 190: 1669).

The above-described peptides, expression vectors, cells, antigen-presenting cells and CTLs of the present invention can be used as an active ingredient of a CTL-inducer, i.e., cancer vaccine, by formulating into an appropriate form depending on the respective substances, as hereinafter described in more detail.

(1) Cancer Vaccine Comprising as an Active Ingredient a Peptide of the Present Invention The peptide of the present invention has a CTL-inducing ability and the so induced CTLs can exert the anti-cancer activity through cytotoxic action or production of lymphokines. The peptide of the present invention therefore can be used as an active ingredient of cancer vaccine for treating or preventing cancer. Thus, the present invention provides cancer vaccine (pharmaceutical composition as cancer vaccine) comprising as an active ingredient a peptide of the present invention. When cancer vaccine of the present invention is administered to an HLA-A26-positive and WT1-positive patient, the peptide (e.g., a cancer antigen peptide consisting of the amino acid sequence set forth in SEQ ID NO: 2, 8, 9, 10, 11, 12, 13, 14 or 15, preferably the amino acid sequence set forth in SEQ ID NO: 2, 8 or 9) is presented to HLA-A26 antigen of antigen-presenting cells. Then, CTLs specifically recognizing the presented HLA-A26 antigen complex can proliferate and destroy the cancer cells, whereby the treatment or prevention of cancer becomes possible. The cancer vaccine of the present invention can be used in the prevention or treatment of cancer accompanied by elevated expression level of WT1 gene, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

Thus, in another embodiment, the present invention provides a method for treatment or prevention of cancer, which comprises administering an effective amount of cancer vaccine of the present invention to an HLA-A26-positive and WT1-positive patient.

The cancer vaccine comprising as an active ingredient a peptide of the present invention may contain a single CTL epitope (e.g., a tumor antigen peptide consisting of the amino acid sequence set forth in SEQ ID NO: 2, 8, 9, 10, 11, 12, 13, 14 or 15, preferably the amino acid sequence set forth in SEQ ID NO: 2, 8 or 9) or an epitope peptide wherein a peptide is ligated with other peptide(s) (CTL epitope, helper epitope, etc.) as an active ingredient. Recently, it has been shown that an epitope peptide wherein multiple CTL epitopes (antigen peptides) are linked has an activity of inducing in vivo CTLs efficiently. For example, it was reported that about 30-mer epitope peptide wherein CTL epitopes (antigen peptides) restricted to HLA-A2-, -A3, -A 11 or B53 originated from cancer antigen protein PSA are ligated induced in vivo CTLs specific for respective CTL epitopes (*Journal of Immunology* 1998, 161: 3186-3194). It has also been reported that an epitope peptide wherein a CTL epitope(s) and a helper epitope(s) are ligated can induce CTLs efficiently. When an epitope peptide in these forms is administered, said peptide is incorporated into antigen-presenting cells; the respective antigen peptides generated by intracellular degradation bind to HLA antigens to form complexes; the complexes are presented on the surface of antigen-presenting cells in high density; and CTLs specific for the complexes efficiently proliferate in the body and destroy cancer cells. In this way, the treatment or prevention of cancer is achieved.

The cancer vaccine comprising as an active ingredient a peptide of the present invention may be administered together with a pharmaceutically acceptable carrier, for example, an appropriate adjuvant, or in the form of particles so that the cellular immunity can be established effectively. As an adjuvant, those described in a literature (*Clin. Microbiol. Rev.*, 7:277-289, 1994), and the like are applicable. Concrete examples include microorganism-derived components, cytokines, plant-derived components, marine organism-derived components, mineral gels such as aluminium hydroxide, surfactants such as lysolecithin and Pluronic polyols, polyanions, peptides, oil emulsion (emulsion preparations) and the like. Liposomal preparations, particulate preparations in which the ingredient is bound to beads having a diameter of several μm, preparations in which the ingredient is attached to lipids, and the like, are also contemplated.

Administration may be achieved, for example, intradermally, subcutaneously, intramuscularly, or intravenously. Although the dosage of the peptide of the present invention in the formulation may be adjusted as appropriate depending on the disease to be treated, the age and the body weight of patient, it is usually within the range of 0.0001 mg-1000 mg, preferably 0.001 mg-1000 mg, more preferably 0.1 mg-10 mg, which can be preferably administered once in every several days to every several months.

(2) DNA Vaccine Comprising as an Active Ingredient an Expression Vector Containing a Polynucleotide Encoding a Peptide of the Present Invention Not only the above-mentioned peptide of the present invention but also an expression vector containing a polynucleotide encoding a peptide of the present invention can be an active ingredient of DNA vaccine for treating or preventing cancer. Thus, the present invention provides cancer vaccine (pharmaceutical composition as cancer vaccine) comprising as an active ingredient an expression vector containing a polynucleotide encoding a peptide of the present invention. In another embodiment, the present invention provides a method of treating or preventing cancer, which comprises administering an effective amount of DNA vaccine of the present invention to an HLA-A26-positive and WT1-positive patient.

Recently, a polynucleotide encoding an epitope peptide wherein multiple (plural) CTL epitopes (antigen peptides) are ligated or wherein a CTL epitope(s) and a helper epitope(s) are ligated has been shown to have an activity of inducing CTLs in vivo efficiently. For example, it is reported that a DNA (minigene) encoding an epitope peptide wherein HBV-originated HLA-A2-restricted antigen peptides (6 peptides), HLA-A11-restricted antigen peptides (3 peptides) and a helper epitope are ligated induced in vivo CTLs directed to the respective epitopes efficiently (*Journal of Immunology* 1999, 162: 3915-3925).

Accordingly, an active ingredient of cancer vaccine can be obtained by incorporating a polynucleotide encoding an epitope peptide of the present invention into an appropriate expression vector.

When administering an expression vector containing a polynucleotide of the present invention as an active ingredient of cancer vaccine (DNA vaccine), the following methods can be used.

As a method for introducing a polynucleotide of the present invention into cells, any means including those utilizing viral vectors or other methods are applicable (*Nikkei-Science*, April, 1994, 20-45; *Gekkan-Yakuji*, 36(1), 23-48 (1994); *Jikken-Igaku-Zokan*, 12(15), 1994, and references cited therein).

Examples of a method utilizing a viral vector include those wherein a DNA of the present invention is incorporated into DNA or RNA virus such as retrovirus, adenovirus, adeno-associated virus, herpes virus, vaccinia virus, poxvirus, poliovirus, or Sindbis virus, and then introduced into cells. Above all, a method using retrovirus, adenovirus, adeno-associated virus, or vaccinia virus, or the like, is particularly preferred.

Examples of other methods include a method wherein an expression plasmid is directly injected intramuscularly (DNA vaccination), liposome method, Lipofectin method, microinjection, calcium phosphate method and electroporation. DNA vaccination and liposome method are preferred.

Regarding a method for allowing the polynucleotide of the present invention to act as a medicament in practice, there are an in vivo method wherein the polynucleotide is directly introduced into the body and an ex vivo method wherein the DNA is introduced extracorporeally into a certain cells removed from human, and the cells are reintroduced into the body (*Nikkei-Science*, April, 1994, 20-45; *Gekkan-Yakuji*, 36(1), 23-48 (1994); *Jikkenn-Igaku-Zokan*, 12(15), 1994; and references cited therein). The in vivo method is more preferred.

In the case of in vivo method, the administration can be effected through any appropriate routes depending on the disease and symptoms to be treated. For example, it may be administered via intravenous, intraarterial, subcutaneous, intracutaneous, intramuscular route, or the like. When the administration is carried out by in vivo method, the composition may be administered in various forms such as solution though, it is typically formulated, for example, into an injection which contains as an active ingredient an expression vector containing a polynucleotide of the present invention. The injection may contain a conventional carriers, if necessary. As for the liposomes or membrane-fused liposomes (such as Sendai virus (HVJ)-liposomes) which contains an expression vector containing a polynucleotide of the present invention, they may be in the form of liposomal formulation such as suspension, frozen drug, centrifugally-concentrated frozen drug, or the like.

Although the content of an expression vector containing a polynucleotide in a formulation may be adjusted as appropriate depending on, for example, the disease to be treated, age and body weight of a patient, usually 0.0001 mg-100 mg, preferably 0.001 mg-10 mg of an expression vector containing a polynucleotide of the present invention can be administered once in every several days to every several months.

When the above-mentioned expression vector containing a polynucleotide of the present invention is administered to a cancer patient, a polypeptide corresponding to the said polynucleotide is highly expressed in antigen-presenting cells. Thereafter, cancer antigen peptides generated by intracellular degradation form complexes with HLA antigens; the complexes are then presented on the surface of antigen-presenting cells in high density; and CTLs specifically recognize said complexes are efficiently proliferate in the body, and destroy cancer cells. In this way, treatment or prevention of cancer is achieved. The cancer vaccine comprising as an active ingredient an expression vector containing a polynucleotide of the present invention can be used in the prevention or treatment of cancer accompanied by elevated expression level of WT1 gene, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(3) Cancer Vaccine Comprising as an Active Ingredient Antigen-Presenting Cells of the Present Invention The present invention provides cancer vaccine comprising as an active ingredient antigen-presenting cells of the present invention.

Recently, a cell therapy (DC therapy) which comprises isolating lymphocytes from peripheral blood of a cancer patient, inducing dendritic cells from the lymphocytes, pulsing the dendritic cells with a peptide or the like in vitro, and reintroducing the resultant antigen-presenting cells into the patient by subcutaneous injection or the like has been reported (*Cancer Immunol. Immunother.*, 46:82, 1998, *J. Immunol.*, 158: p 1796, 1997, *Cancer Res.*, 59: p 1184, 1999, *Cancer Res.*, 56: p 5672, 1996, *J. Immunol.*, 161: p 5607, 1998, *J. Exp. Med.*, 184: p 465, 1996). The above-described antigen-presenting cells of the present invention therefore can be used as an active ingredient of cancer vaccine to be used in the cell therapy.

The cancer vaccine comprising as an active ingredient antigen-presenting cells of the present invention preferably contains physiological saline, phosphate buffered saline (PBS), medium, or the like, to stably maintain the antigen-presenting cells. It may be administered, for example, intravenously, subcutaneously, or intradermally. The dose is similar to that described in the references cited above.

When the cancer vaccine above is reintroduced into a patient's body, specific CTLs are efficiently induced in the body of a patient positive for HLA-A26 and positive for WT1, whereby treatment or prevention of cancer can be effected. The cancer vaccine comprising as an active ingredient antigen-presenting cells of the present invention can be used in the prevention or treatment of cancer accompanied by elevated expression level of WT1 gene, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

(4) Cancer Vaccine Comprising as an Active Ingredient CTLs of the Present Invention The present invention provides cancer vaccine (pharmaceutical composition as cancer vaccine) comprising as an active ingredient CTLs of the present invention. CTLs of the present invention can be used effectively in the adoptive immunotherapy as hereinafter described.

In melanomas, therapeutic effect has been observed in adoptive immunotherapy wherein tumor-infiltrating T cells are removed from a patient and cultured ex vivo in large quantities, and returned into the same patient (*J. Natl. Cancer. Inst.*, 86: 1159, 1994). Further, in mouse melanoma, suppression of metastasis has been observed when splenocytes were stimulated with cancer antigen peptide TRP-2 in vitro to amplify CTLs specific for the cancer antigen peptide, and the CTLs are administered to a melanoma-grafted mouse (*J. Exp. Med.*, 185:453, 1997). This resulted from in vitro proliferation of CTLs that specifically recognize a complex between an HLA antigen of antigen-presenting cells and a cancer antigen peptide. Accordingly, a therapeutic method comprising stimulating in vitro peripheral blood lymphocytes from a patient with a peptide, or a polynucleotide or an expression vector of the present invention to proliferate cancer-specific CTLs, and returning the CTLs into the patient is believed to be effective. Thus, the CTLs of the present invention can be used as an active ingredient of cancer vaccine in the adoptive immunotherapy.

The cancer vaccine comprising as an active ingredient CTLs of the present invention preferably contains physiological saline, phosphate buffered saline (PBS), medium, or the like to stably maintain CTLs. It may be administered, for example, intravenously, subcutaneously or intradermally. The dose is similar to that described in the references cited above.

When the cancer vaccine is returned to a patient positive for HLA-A26 and positive for WT1, the cytotoxic action of CTLs on cancer cells is enhanced in the body of a patient, and the cancer cells are destroyed. In this way, cancer can be treated. The cancer vaccine comprising as an active ingredient CTLs of the present invention can be used in the prevention or treatment of cancer accompanied by elevated expression level of WT1 gene, for example, blood cancers such as leukemia, myelodysplastic syndrome, multiple myeloma and malignant lymphoma, and solid cancers such as gastric cancer, colon cancer, lung cancer, breast cancer, embryonal cancer, hepatic cancer, skin cancer, bladder cancer, prostate cancer, uterine cancer, cervical cancer, and ovarian cancer.

The present invention also provides an HLA monomer, an HLA dimer, an HLA tetramer or an HLA pentamer comprising a cancer antigen peptide of the present invention and HLA-A26 antigen.

In the cancer immunotherapy, examination of the frequency or amount of CTL precursor cells directed to a cancer antigen (cancer antigen peptide) in a patient before treatment, or examination of the frequency or amount of CTLs in a patient during treatment with a cancer antigen (cancer antigen peptide) can provide a significant indicator in the selection of patients highly responsive to the cancer antigen (cancer antigen peptide), the monitoring of therapeutic effects, or the evaluation of suitability of treatment. An HLA monomer, an HLA dimer, an HLA tetramer and an HLA pentamer each comprising a tumor antigen peptide together with an HLA antigen are useful as a reagent in the detection of CTLs specific for antigen (antigen peptide), specifically, in the measurement of frequency or amount of CTLs.

As used herein, the HLA tetramer refers to a tetramer prepared by biotinylating a complex (HLA monomer) obtained by association of an HLA antigen α-chain and a β2-microglobulin with a peptide (antigen peptide), and allowing to bind to avidin for tetramerization (*Science* 279: 2103-2106 (1998); and *Science* 274: 94-96 (1996)).

The HLA monomer is a monomer that is used in the preparation of the above-mentioned HLA tetramer and is formed by biotinylating an association of HLA antigen α-chain, β2-microglobulin and antigen peptide.

The HLA dimer is a dimer prepared by fusing HLA antigen α-chain and Ig (immunoglobulin, for example, IgG1), and binding the resultant fusion to β2-microglobulin and antigen peptide (*Proc. Natl. Acad. Sci. USA* 90: 6671-6675 (1993)). The antigen peptide-specific CTLs bound to HLA dimer can be detected by, for example, allowing labeled anti-IgG1 antibody to bind to IgG1.

The HLA pentamer is a recently developed technique and refers to a pentamer wherein five molecules of a complex comprising HLA antigen and antigen peptide are polymerized through Coiled-Coil domain. Since the HLA antigen-antigen peptide complex can be labeled with fluorescence or the like, the analysis can be carried out by flow cytometry or the like similarly to HLA tetramer.

The aforementioned HLA-monomer, dimer, tetramer and pentamer are all available by custom production from a manufacture such as ProImmune or BD Biosciences. At present, HLA tetramers and the like which comprise different antigen peptides are commercially available (Medical & Biological Laboratories Co., Ltd., etc.)

Examples of the HLA monomer, dimer, tetramer and pentamer of the present invention, specifically, include HLA monomers, dimers, tetramers and pentamers each comprising a peptide consisting of the amino acid sequence set forth in SEQ ID NO: 2, 8, 9, 10, 11, 12, 13, 14 or 15, preferably the amino acid sequence set forth in SEQ ID NO: 2, 8 or 9 and an HLA-A26 antigen. Preferably, an HLA tetramer or HLA pentamer and more preferably, an HLA tetramer is used in the detection of CTLs.

The HLA monomer, HLA tetramer and HLA pentamer are preferably labeled with fluorescence so that the bound CTLs can be easily sorted out or detected by a known detection measure such as flow cytometry, fluorescent microscopy, and the like. Examples include HLA monomers, tetramers and pentamers labeled with phycoerythrin(PE), fluorescein isothiocyanate (FITC), peridinyl chlorophyll protein (PerCP), allophycocyanin (APC), or the like.

The HLA-A26 antigen (HLA-A26 antigen α-chain) which is a component of the HLA monomer, dimer, tetramer and pentamer of the present invention can be cloned easily by a conventional method such as PCR on the basis of information about known base sequence of HLA-A26 and the like disclosed in Genbank Accession No. D14350.

The β2-microglobulin which is a component of the HLA monomer, dimer, tetramer and pentamer of the present invention is preferably originated from human. The human β2-microglobulin can be cloned easily by a conventional method such as PCR on the basis of information about known base sequence of human β2-microglobulin disclosed in GenBank Acc. No. AB021288.

The process for the preparation of HLA monomer, dimer, tetramer and pentamer is well known from the respective literatures mentioned above; however, the preparation will be hereinafter described briefly regarding HLA tetramer.

First, an appropriate host cell such as E. coli or mammalian cells capable of expressing a protein is transformed with an HLA-A26 α-chain expression vector and a β2-microglobulin expression vector, and allowed to express. E. coli (e.g., BL21) is preferably used here. The resultant monomer HLA-A26 complex and a peptide of the present invention are then mixed to form a soluble HLA-peptide complex. The C-terminal sequence of HLA-A26 α-chain of the resultant HLA-peptide complex is biotinylated with BirA enzyme. When a biotinylated HLA-peptide complex and a fluorescently labeled avidin are mixed at the molar ratio of 4:1, an HLA tetramer is formed. It is preferred to purify the resulting protein by gel filtration or the like in each step above.

The HLA monomer, dimer, tetramer and pentamer described above are used effectively as a detecting agent for CTLs which are specific for HLA-A26-binding cancer antigen peptides.

The CTL-detecting agent of the present invention can be used for the following purposes, for example.

1) It can be used to examine the frequency or amount of CTL precursors directed to a cancer antigen peptide of the present invention before treatment with the cancer antigen peptide. This makes it possible to evaluate the responsiveness of a patient to the cancer antigen peptide.

2) It can be used to examine the frequency or amount of CTLs in a patient during treatment with a cancer antigen peptide of the present invention. This makes it possible to monitor the therapeutic effects, evaluate the suitability of treatment, and confirm that treatment proceeds favorably, and the like.

Detection of CTLs can be carried out by, specifically, isolating a biological sample (e.g., PBMC) containing CTLs from a subject patient, bringing an HLA tetramer or the like of the present invention into contact with the biological sample, and measuring the existing frequency or amount of CTLs specific for the peptide of the present invention bound to the HLA tetramer or the like by flow cytometry, or the like.

The present inventors also found for the first time that a peptide comprising the amino acid sequence of Asp Leu Asn Ala Leu Leu Pro Ala Val (SEQ ID NO: 3) is an HLA-A*0201-binding cancer antigen peptide. Although the peptide sequence set forth in SEQ ID NO: 3 has been disclosed in WO 00/18795, the following findings have been for the first time disclosed by the present invention: said peptide has an activity as an HLA-A*0201-binding cancer antigen peptide, said peptide is generated by intracellular processing of WT1 protein, a complex of said peptide with an HLA-A*0201 antigen is presented on the cell surface and recognized by CTLs, and said peptide is a therapeutically effective cancer antigen peptide.

Thus, the present invention provides a pharmaceutical composition comprising any one of the following a) to f):

a) a peptide comprising the amino acid sequence set forth in SEQ ID NO: 3, b) an epitope peptide comprising the peptide of a) above, c) an expression vector containing a polynucleotide encoding the peptide of a) or b) above, d) a cell containing the expression vector of c) above, e) an antigen-presenting cell on which a complex between the peptide of a) above and an HLA-A*0201 antigen is presented, and f) a CTL which recognizes a complex between the peptide of a) above and an HLA-A*0201 antigen, together with a pharmaceutically acceptable carrier.

Regarding an HLA-A2 antigen such as HLA-A*0201 antigen, a certain rules (binding motifs) in the sequence of an antigen peptide capable of binding to said HLA antigen and being presented are known. That is, the binding motif for HLA-A2-binding peptide is known that, in the peptides consisting of 8-11 amino acid, the amino acid residue at position 2 is leucine, methionine, valine, isoleucine or glutamine, and the amino acid at the C-terminus is valine or leucine (*Immunogenetics*, 41, p 178, 1995, *J. Immunol.*, 155: p 4749, 1995). Accordingly, the amino acid residue at the position 2 and/or the C-terminus of the above-mentioned peptide shown in SEQ ID NO: 3 can be substituted by another amino acid residue available in view of the above-mentioned motifs. Thus, not only the peptide shown in SEQ ID NO: 3 but also a variant set forth in SEQ ID NO: 4 which is under the rule of the above-mentioned motifs (with the proviso the a peptide shown in SEQ ID NO: 3 is excluded) can be used in a pharmaceutical composition similar to the above as long as said variant has an activity of cancer antigen peptide.

Thus, the present invention provides a pharmaceutical composition comprising any one of the following a)' to f)':

a)' a cancer antigen peptide comprising the amino acid sequence set forth in SEQ ID NO: 4, b)' an epitope peptide comprising the peptide of a)' above, c)' an expression vector containing a polynucleotide encoding the peptide of a)' or b)' above, d)' a cell containing the expression vector of c)' above, e)' an antigen-presenting cell on which a complex between the peptide of a)' above and an HLA-A*0201 antigen is presented, and f)' a CTL which recognizes a complex between the peptide of a)' above and an HLA-A*0201 antigen, together with a pharmaceutically acceptable carrier.

The method for preparing or measuring activity of the respective substances described in a)-f) and a)'-f)', and their use as a CTL inducer or cancer vaccine are the same as those described in regard to the peptide of the present invention which has activity as an HLA-A26-bindng cancer antigen peptide. However, the peptide set forth in SEQ ID NO: 3 or 4 is used in place the peptide set forth in SEQ ID NO: 2, 8, 9, 10, 11, 12, 13, 14 or 15 and that HLA-A*0201 antigen is used in place of HLA-A26 antigen. The HLA-A*0201 antigen is known in Genbank Accession No. M84379.

The present invention also provides an HLA monomer, an HLA dimer, an HLA tetramer or an HLA pentamer comprising a peptide having the amino acid sequence of Asp Leu Asn Ala Leu Leu Pro Ala Val set forth in SEQ ID NO: 3, and an HLA-A*0201 antigen; and a detecting agent for CTLs which are specific for WT1-derived HLA-A*0201-binding cancer antigen peptide comprising the same as an ingredient. The description provided above in regard to a peptide having activity as an HLA-A26-binding cancer antigen peptide is applicable to these HLA monomer, HLA dimer, HLA tetramer and HLA pentamer, and CTL-detecting agent. However, the peptide set forth in SEQ ID NO: 3 or 4 is used in place of the peptide set forth in SEQ ID NO: 2, 8, 9, 10, 11, 12, 13, 14 or 15 and that HLA-A*0201 antigen is used in place of HLA-A26 antigen.

EXAMPLES

The present invention is further illustrated by the following examples, but is not limited by these examples in any respect.

Example 1

Identification of HLA-A*0201-Binding Antigen Peptides

A peptide having an amino acid sequence set forth in SEQ ID NO: 3 which corresponds to the one at position 7-15 of human WT1 amino acid sequence (*Cell* 60: 509, 1990, SEQ ID NO: 1) was synthesized by solid-phase synthesis.

After obtaining informed-consent, blood was collected from HLA-A*0201-positive healthy subjects and peripheral blood mononuclear cells (PBMCs) were isolated using Ficoll-Hypaque separation solution. HLA-A*0201-positive T2 cell lines incapable of presenting endogenous peptides to HLA due to deficit in TAP gene (*J. Immunol.* 150: 1763, 1993) were pulsed with the peptide of SEQ ID NO: 3 at 20 μM for 2 hours, then radiated (7500 cGy), and co-cultured with PBMCs at the cell number ratio of 1:1. As the culture solution, a complete medium composed of 45% AIM-V medium, 45% RPMI1640 medium, 10% inactivated human serum, 0.1 mM MEM non-essential amino acids, 100 ng/mL streptomycin, 100 IU/mL penicillin and 25 ng/mL 2-mercaptoethanol was used. Seven days later, the second-time stimulation was conducted in a similar manner, and thereto was added 25 IU/mL of IL-2 (Shionogi & Co., Ltd) on the next day. Stimulation was conducted five times in total, and effector cells obtained after 5 days from the last stimulation were used in the measurement of cytotoxicity.

The cytotoxic activity of CTLs on target cells was measured by $^{51}$Cr-release assay. The $^{51}$Cr-labeled target cells ($1 \times 10^4$ cells/100 μL in total) were cocultured with different numbers of effector cells (100 μL) in a round-bottom 96-well plate. After culturing at 37° C. for 3-5 hours, the plate was centrifuged to separate the supernatant (100 μL) which was subjected to the measurement of γ ray. Specific cytotoxicity (% specific lysis) was calculated as follows:

% specific lysis=(*cpm* experimental release–*cpm* spontaneous release)/(*cpm* maximal release–*cpm* spontaneous release)×100

Figure 1:
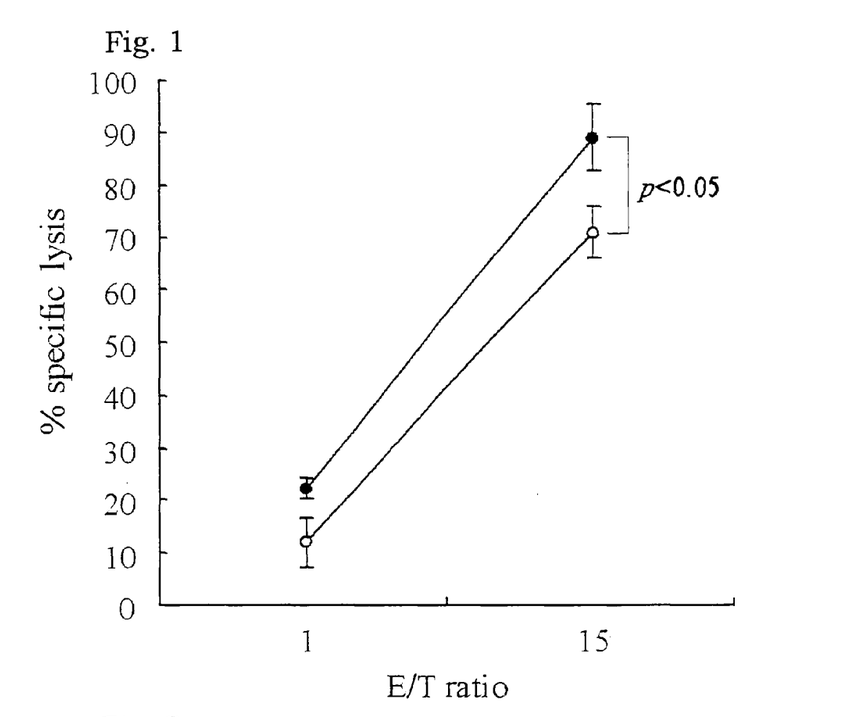
FIG. 1 is a graph showing the results of experiments where the cytotoxic activity of CTLs induced by stimulation with a peptide of SEQ ID NO: 3 on T2 target cells either pulsed (filled circle) or not-pulsed (open circle) with the peptide was examined. In the figure, the vertical axis indicates the specific cytotoxic activity (% specific lysis) and the abscissa axis the E/T ratio which is a ratio of effector cell number (E) to target cell number (T).

The "spontaneous release" and the "maximal release" were measured in the supernatant obtained from the culture of target cells and that obtained from the culture of target cells treated with 1% Triton X-100 solution, respectively. The significant difference test was conducted by Student's t-test. The cytotoxic activity was measured using, as target cells, T2 cells pulsed with the same peptide as used in the stimulation or T2 cells not pulsed with the peptide. The results are shown in FIG. 1. CTLs induced by stimulation with T2 cells pulsed with the peptide of SEQ ID NO: 3 exerted more potent cytotoxic activity on T2 cells pulsed with the peptide than on T2 cells not-pulsed with the peptide (p<0.05). These results demonstrated that CTLs specifically recognize the WT1-derived peptide of SEQ ID NO: 3 are induced from HLA-A*0201-positive human PBMCs by stimulation with the peptide of SEQ ID NO: 3.

Figure 2:
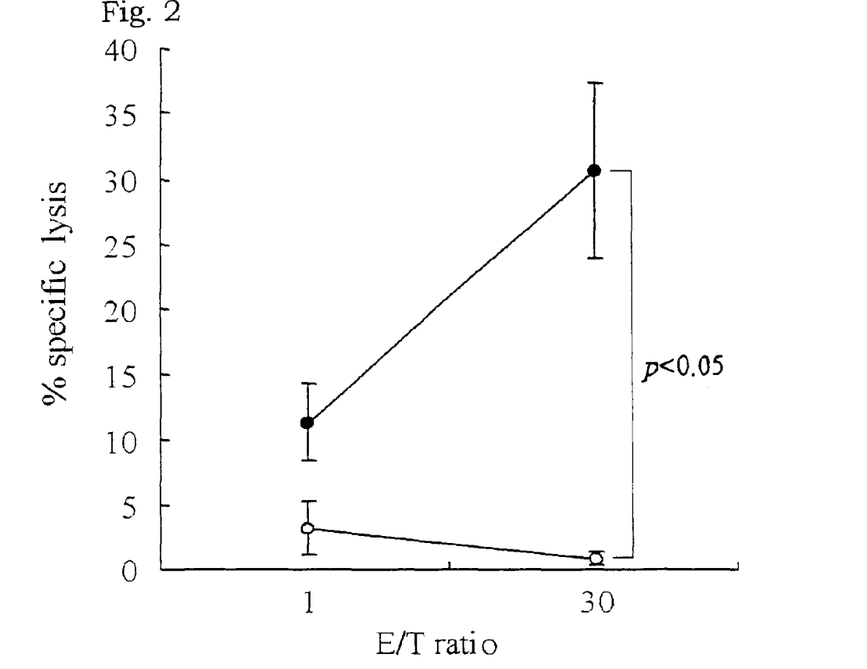
FIG. 2 is a graph showing the results of experiments where the cytotoxic activity of CTLs induced by stimulation with a peptide of SEQ ID NO: 3 on TF-1 cell line (filled circle), which is positive for HLA-A*0201 and expresses WT1, or JY cell line (open circle), which is positive for HLA-A*0201 and not expresses WT1, was examined. In the figure, the vertical axis indicates the specific cytotoxic activity (% specific lysis) and the abscissa axis the E/T ratio.

Then, the cytotoxic activity of CTLs induced by the peptide of SEQ ID NO: 3 on TF-1 and JY cell lines was examined, wherein the TF-1 cell line is positive for HLA-A*0201 and expresses WT1 (*J. Cell. Physiol.* 140: 323, 1989), while the JY cell line is positive for HLA-A*0201 but does not express WT1 (*J. Biol. Chem.* 252, 1997). The results are shown in FIG. 2. CTLs induced by stimulation with the peptide of SEQ ID NO: 3 killed TF-1 cells and not JY cells (p<0.05). These results demonstrated that a peptide of SEQ ID NO: 3 is produced through the processing of intracellularly expressed endogenous WT1 protein, presented as an antigen together with an HLA-A*0201 molecule, and recognized by CTLs.

Example 2

Identification of Antigen Peptides Binding to HLA-A26 (1)

A peptide shown in SEQ ID NO: 2 which corresponds to the position 368-376 of amino acid sequence of human WT1 (*Cell*, 60:509, 1990, SEQ ID NO: 1) was synthesized by solid state synthesis.

Figure 3:
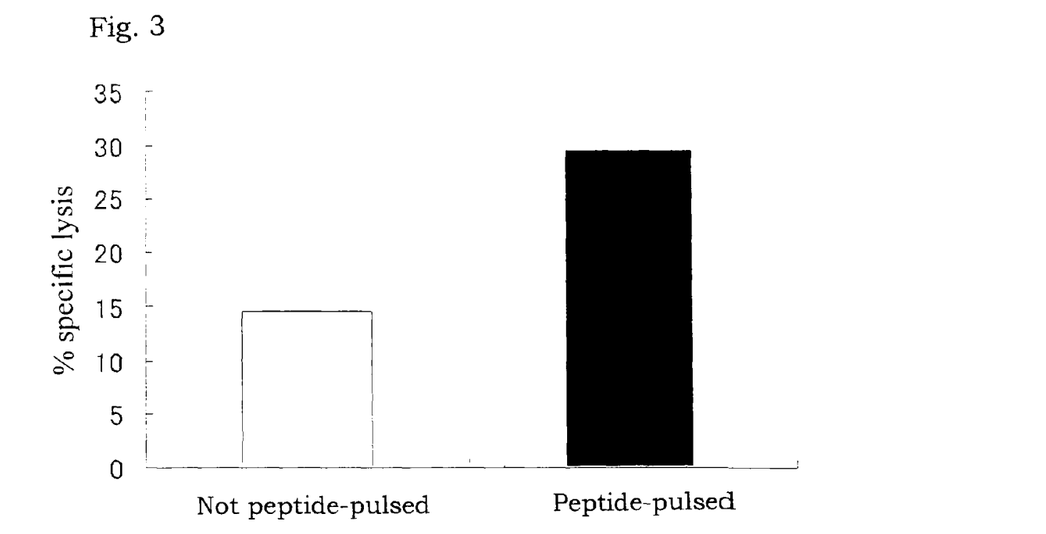
FIG. 3 is a graph showing the results of experiments where the cytotoxic activity of CTLs induced by stimulation with a peptide of SEQ ID NO: 2 on B-LCL target cells either pulsed (solid bar) or not-pulsed (open bar) with the peptide was examined. In the figure, the vertical axis indicates the specific cytotoxic activity (% specific lysis).

After obtaining informed consent, PBMCs were prepared from HLA-A26-positive healthy subject in a similar manner to Example 1, and stimulated by adding the peptide of SEQ ID NO: 2. One week later, PBMCs were pulsed with the peptide of SEQ ID NO: 2, and used as stimulators in the stimulation. The stimulation was conducted every one week 4 times in total. One week later, B cells (B-LCL) transformed with EB virus were pulsed with the peptide of SEQ ID NO: 2, and used as stimulators in the stimulation. After 5 days from the final stimulation, the cytotoxic activity was measured by $^{51}$Cr-release assay in a similar manner to Example 1 using, as target cells, B-LCL cells pulsed with the peptide of SEQ ID NO: 2 and B-LCL cells not-pulsed with the peptide. The results are shown in FIG. 3. CTLs induced by stimulation with the peptide of SEQ ID NO: 2 exerted more potent cytotoxic activity on B-LCL cells pulsed with the peptide than on B-LCL cells not-pulsed with the peptide. These results demonstrated that CTLs specifically recognize the WT1-derived peptide of SEQ ID NO: 2 are induced from HLA-A26-positive human PBMCs by stimulation with the peptide of SEQ ID NO: 2.

The genotype of HLA-A26-positive healthy subject used herein is known be HLA-A*2601.

Example 3

Identification of Antigen Peptides Binding to HLA-A26 (2)

Peptides shown in SEQ ID NOS: 8, 9 and 2 which correspond to the position 152-160, 185-193 and 368-376, respectively, of amino acid sequence of human WT1 (*Cell*, 60: 509, 1990, SEQ ID NO: 1) were synthesized by solid state synthesis.

Figure 4:
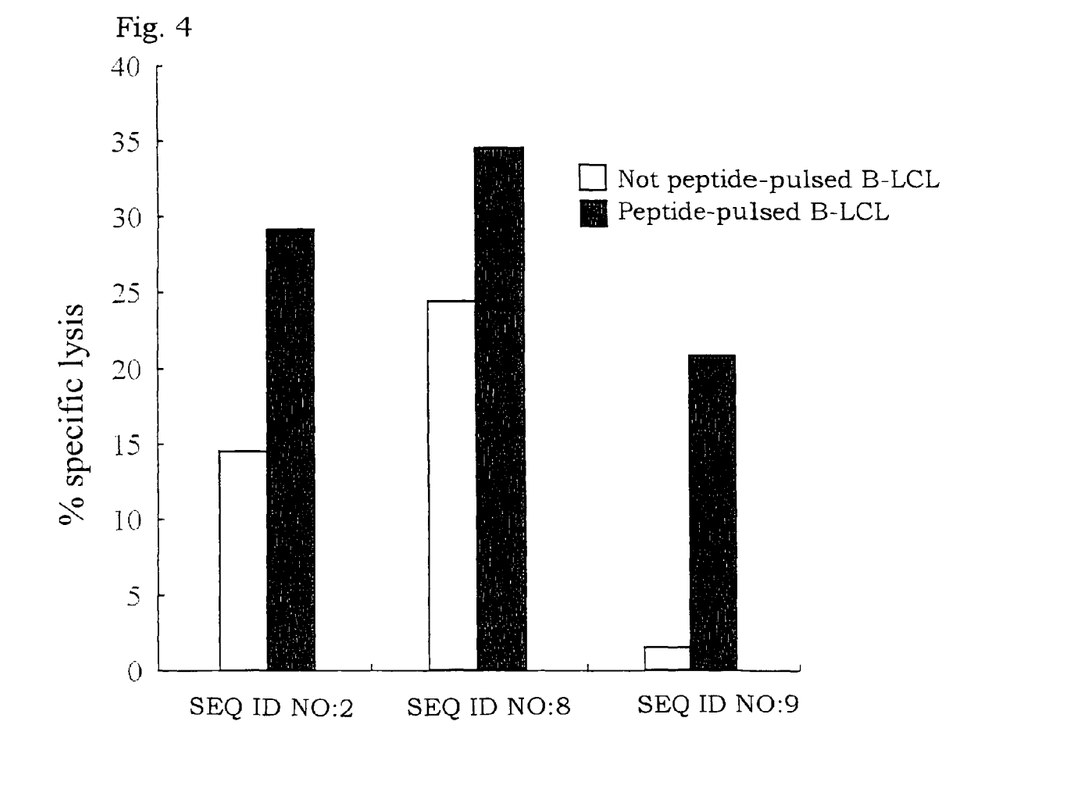
FIG. 4 is a graph showing the results of experiments where the cytotoxic activity of CTLs induced by stimulation with a peptide of SEQ ID NO: 2, 8 or 9 on B-LCL target cells either pulsed (solid bar) or not-pulsed (open bar) with the peptide was examined. In the figure, the vertical axis indicates the specific cytotoxic activity (% specific lysis).

After obtaining informed consent, PBMCs were prepared from HLA-A26-positive healthy subject in a similar manner to Example 1, and stimulated by adding a peptide of SEQ ID NO: 8. One week later, PBMCs were pulsed with the peptide of SEQ ID NO: 8, and used as stimulators in the stimulation. The stimulation was conducted every one week 3 times in total. After 3 times of stimulation, CD8-positive cells were enriched by negative selection method. Further, stimulation with the peptide of SEQ ID NO: 8 was conducted 2 times. After 5 days from the final stimulation, the cytotoxic activity was measured by $^{51}$Cr-release assay in a similar manner to Example 1 using, as target cells, B-LCL cells pulsed with the peptide of SEQ ID NO: 8 and B-LCL cells not-pulsed with the peptide. Experiments were carried out in the same manner as above using a peptide of SEQ ID NO: 9 and a peptide of SEQ ID NO: 2. The results are shown in FIG. 4. CTLs induced by stimulation with the peptide of SEQ ID NO: 8, the peptide of SEQ ID NO: 9 or the peptide of SEQ ID NO: 2 exerted more potent cytotoxic activity on B-LCL cells pulsed with the peptide than on B-LCL cells not-pulsed with the peptide. These results demonstrated that CTLs specifically recognize the WT1-derived peptide of SEQ ID NO: 8, 9 and 2 are induced from HLA-A26-positive human PBMCs by stimulation with the peptide of SEQ ID NO: 8, 9 and 2, respectively.

INDUSTRIAL APPLICABILITY

Cancer antigen peptides derived from WT1, polynucleotides encoding the same, CTL-inducers comprising the same, and the like are provided by the present invention. The CTL inducer of the present invention is useful as cancer vaccine. The cancer vaccine of the present invention is applicable to many cancer patients who are positive for HLA-A26 or HLA-A*0201.

Sequence Listing Free Text

The amino acid sequence set forth in SEQ ID NO: 2 is a synthetic peptide.

The amino acid sequence set forth in SEQ ID NO: 3 is a synthetic peptide.

In the amino acid sequence set forth in SEQ ID NO: 4, the second amino acid is leucine, methionine, valine, isoleucine or glutamine and the ninth amino acid is valine or leucine.

The amino acid sequence set forth in SEQ ID NO: 5 is a synthetic peptide.

The amino acid sequence set forth in SEQ ID NO: 6 is a synthetic peptide.

The amino acid sequence set forth in SEQ ID NO: 7 is a synthetic peptide.

The amino acid sequence set forth in SEQ ID NO: 8 is a synthetic peptide.

The amino acid sequence set forth in SEQ ID NO: 9 is a synthetic peptide.

The amino acid sequence set forth in SEQ ID NO: 10 is a synthetic peptide.

The amino acid sequence set forth in SEQ ID NO: 11 is a synthetic peptide.

The amino acid sequence set forth in SEQ ID NO: 12 is a synthetic peptide.

The amino acid sequence set forth in SEQ ID NO: 13 is a synthetic peptide.

The amino acid sequence set forth in SEQ ID NO: 14 is a synthetic peptide.

The amino acid sequence set forth in SEQ ID NO: 15 is a synthetic peptide.

The invention claimed is:

1. A method for treating cancer in an HLA-A26 positive patient, said method comprising inducing CTL that specifically recognize a complex of an HLA-A26 antigen and a peptide as set forth in any one of SEQ ID NOs: 2, 8, and 9, by administering an effective amount of a peptide as set forth in any one of SEQ ID NOs: 2, 8, and 9 to an HLA-A26 positive patient to contact peripheral blood mononuclear cells of said HLA-A26 positive subject with said peptide as set forth in any one of SEQ ID NOs: 2, 8, and 9.

2. A method according to claim 1, wherein said patient is positive for WT1.

3. A method according to claim 1, wherein said peptide is SEQ ID NO: 2.

4. A method according to claim 1, wherein said peptide is SEQ ID NO: 8.

5. A method according to claim 1, wherein said peptide is SEQ ID NO: 9.

6. A method according to claim 1, wherein said cancer is at least one selected from the group consisting of leukemia, myelodysplastic syndrome, multiple myeloma, malignant lymphoma, gastric cancer, colon cancer, lung cancer, breast cancer, embryonal cancer, hepatic cancer, skin cancer, bladder cancer, prostate cancer, uterine cancer, cervical cancer, and ovarian cancer.

* * * * *

SEQUENCE LISTING

```
<160> NUMBER OF SEQ ID NOS: 15

<210> SEQ ID NO 1
<211> LENGTH: 449
<212> TYPE: PRT
<213> ORGANISM: Homosapiens

<400> SEQUENCE: 1

Met Gly Ser Asp Val Arg Asp Leu Asn Ala Leu Leu Pro Ala Val Pro
1               5                   10                  15

Ser Leu Gly Gly Gly Gly Gly Cys Ala Leu Pro Val Ser Gly Ala Ala
                20                  25                  30

Gln Trp Ala Pro Val Leu Asp Phe Ala Pro Pro Gly Ala Ser Ala Tyr
            35                  40                  45

Gly Ser Leu Gly Gly Pro Ala Pro Pro Ala Pro Pro Pro Pro
        50                  55                  60

Pro Pro Pro Pro His Ser Phe Ile Lys Gln Glu Pro Ser Trp Gly Gly
65                  70                  75                  80

Ala Glu Pro His Glu Glu Gln Cys Leu Ser Ala Phe Thr Val His Phe
                85                  90                  95

Ser Gly Gln Phe Thr Gly Thr Ala Gly Ala Cys Arg Tyr Gly Pro Phe
            100                 105                 110

Gly Pro Pro Pro Ser Gln Ala Ser Ser Gly Gln Ala Arg Met Phe
        115                 120                 125

Pro Asn Ala Pro Tyr Leu Pro Ser Cys Leu Glu Ser Gln Pro Ala Ile
            130                 135                 140

Arg Asn Gln Gly Tyr Ser Thr Val Thr Phe Asp Gly Thr Pro Ser Tyr
145                 150                 155                 160

Gly His Thr Pro Ser His His Ala Ala Gln Phe Pro Asn His Ser Phe
```

-continued

```
                165                 170                 175
Lys His Glu Asp Pro Met Gly Gln Gln Gly Ser Leu Gly Glu Gln Gln
            180                 185                 190

Tyr Ser Val Pro Pro Val Tyr Gly Cys His Thr Pro Thr Asp Ser
            195                 200                 205

Cys Thr Gly Ser Gln Ala Leu Leu Arg Thr Pro Tyr Ser Ser Asp
            210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Val Ala Ala Gly Ser Ser Ser
                245                 250                 255

Ser Val Lys Trp Thr Glu Gly Gln Ser Asn His Ser Thr Gly Tyr Glu
            260                 265                 270

Ser Asp Asn His Thr Thr Pro Ile Leu Cys Gly Ala Gln Tyr Arg Ile
            275                 280                 285

His Thr His Gly Val Phe Arg Gly Ile Gln Asp Val Arg Arg Val Pro
            290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
            340                 345                 350

Tyr Gln Cys Asp Phe Lys Asp Cys Glu Arg Arg Phe Ser Arg Ser Asp
            355                 360                 365

Gln Leu Lys Arg His Gln Arg Arg His Thr Gly Val Lys Pro Phe Gln
            370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415

Arg Trp Pro Ser Cys Gln Lys Lys Phe Ala Arg Ser Asp Glu Leu Val
            420                 425                 430

Arg His His Asn Met His Gln Arg Asn Met Thr Lys Leu Gln Leu Ala
            435                 440                 445

Leu
```

<210> SEQ ID NO 2
<211> LENGTH: 9
<212> TYPE: PRT
<213> ORGANISM: Artificial
<220> FEATURE:
<223> OTHER INFORMATION: Synthetic peptide

<400> SEQUENCE: 2

```
Asp Gln Leu Lys Arg His Gln Arg Arg
1               5
```

<210> SEQ ID NO 3
<211> LENGTH: 9
<212> TYPE: PRT
<213> ORGANISM: Artificial
<220> FEATURE:
<223> OTHER INFORMATION: Synthetic peptide

<400> SEQUENCE: 3

```
Asp Leu Asn Ala Leu Leu Pro Ala Val
1               5
```

```
<210> SEQ ID NO 4
<211> LENGTH: 9
<212> TYPE: PRT
<213> ORGANISM: Artificial
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Leu, Met, Val, Ile, or Gln
<220> FEATURE:
<221> NAME/KEY: MISC_FEATURE
<222> LOCATION: (9)..(9)
<223> OTHER INFORMATION: Xaa is Val or Leu

<400> SEQUENCE: 4

Asp Xaa Asn Ala Leu Leu Pro Ala Xaa
1               5

<210> SEQ ID NO 5
<211> LENGTH: 16
<212> TYPE: PRT
<213> ORGANISM: Artificial
<220> FEATURE:
<223> OTHER INFORMATION: Synthetic peptide

<400> SEQUENCE: 5

Lys Arg Tyr Phe Lys Leu Ser His Leu Gln Met His Ser Arg Lys His
1               5                   10                  15

<210> SEQ ID NO 6
<211> LENGTH: 21
<212> TYPE: PRT
<213> ORGANISM: Artificial
<220> FEATURE:
<223> OTHER INFORMATION: Synthetic peptide

<400> SEQUENCE: 6

Phe Asn Asn Phe Thr Val Ser Phe Trp Leu Arg Val Pro Lys Val Ser
1               5                   10                  15

Ala Ser His Leu Glu
            20

<210> SEQ ID NO 7
<211> LENGTH: 16
<212> TYPE: PRT
<213> ORGANISM: Artificial
<220> FEATURE:
<223> OTHER INFORMATION: Synthetic peptide

<400> SEQUENCE: 7

Ala Gln Tyr Ile Lys Ala Asn Ser Lys Phe Ile Gly Ile Thr Glu Leu
1               5                   10                  15

<210> SEQ ID NO 8
<211> LENGTH: 9
<212> TYPE: PRT
<213> ORGANISM: Artificial
<220> FEATURE:
<223> OTHER INFORMATION: Synthetic peptide

<400> SEQUENCE: 8

Val Thr Phe Asp Gly Thr Pro Ser Tyr
1               5

<210> SEQ ID NO 9
<211> LENGTH: 9
```

```
<212> TYPE: PRT
<213> ORGANISM: Artificial
<220> FEATURE:
<223> OTHER INFORMATION: Synthetic peptide

<400> SEQUENCE: 9

Gln Gly Ser Leu Gly Glu Gln Gln Tyr
1               5

<210> SEQ ID NO 10
<211> LENGTH: 9
<212> TYPE: PRT
<213> ORGANISM: Artificial
<220> FEATURE:
<223> OTHER INFORMATION: Synthetic peptide

<400> SEQUENCE: 10

Phe Ala Pro Pro Gly Ala Ser Ala Tyr
1               5

<210> SEQ ID NO 11
<211> LENGTH: 9
<212> TYPE: PRT
<213> ORGANISM: Artificial
<220> FEATURE:
<223> OTHER INFORMATION: Synthetic peptide

<400> SEQUENCE: 11

Pro Ile Leu Cys Gly Ala Gln Tyr Arg
1               5

<210> SEQ ID NO 12
<211> LENGTH: 10
<212> TYPE: PRT
<213> ORGANISM: Artificial
<220> FEATURE:
<223> OTHER INFORMATION: Synthetic peptide

<400> SEQUENCE: 12

Gly Val Phe Arg Gly Ile Gln Asp Val Arg
1               5                   10

<210> SEQ ID NO 13
<211> LENGTH: 9
<212> TYPE: PRT
<213> ORGANISM: Artificial
<220> FEATURE:
<223> OTHER INFORMATION: Synthetic peptide

<400> SEQUENCE: 13

Cys Leu Glu Ser Gln Pro Ala Ile Arg
1               5

<210> SEQ ID NO 14
<211> LENGTH: 9
<212> TYPE: PRT
<213> ORGANISM: Artificial
<220> FEATURE:
<223> OTHER INFORMATION: Synthetic peptide

<400> SEQUENCE: 14

Lys Arg Tyr Phe Lys Leu Ser His Leu
1               5

<210> SEQ ID NO 15
<211> LENGTH: 9
<212> TYPE: PRT
<213> ORGANISM: Artificial
```

```
<220> FEATURE:
<223> OTHER INFORMATION: Synthetic peptide

<400> SEQUENCE: 15

Ala Leu Leu Pro Ala Val Pro Ser Leu
1               5
```